United States Patent [19]

Murakami

[11] Patent Number: 5,580,162
[45] Date of Patent: Dec. 3, 1996

[54] LIGHTING DEVICE FOR AN OBSERVATION/IMAGE PICKUP APPARATUS

[75] Inventor: Hajime Murakami, Chigasaki, Japan

[73] Assignee: Mitsubishi Chemical Corporation, Tokyo, Japan

[21] Appl. No.: 536,276

[22] Filed: Sep. 29, 1995

[30] Foreign Application Priority Data

Sep. 30, 1994 [JP] Japan .................................. 6-259794
Feb. 6, 1995 [JP] Japan .................................. 7-039413
Feb. 6, 1995 [JP] Japan .................................. 7-039414

[51] Int. Cl.$^6$ ................................................ F21V 29/00
[52] U.S. Cl. ............................ 362/268; 362/283; 362/322
[58] Field of Search ................................. 362/268, 283, 362/32, 322

[56] References Cited

U.S. PATENT DOCUMENTS

| | | | |
|---|---|---|---|
| 2,097,762 | 11/1937 | Heine | 359/386 |
| 4,585,315 | 4/1986 | Sincerbox et al. | 359/387 |
| 4,705,366 | 11/1987 | Kimura et al. | 350/529 |
| 5,220,453 | 6/1993 | McKinley et al. | 362/268 |
| 5,351,169 | 9/1994 | Ishikawa et al. | 362/32 |

Primary Examiner—Denise L. Cromada
Assistant Examiner—Alfred Basichas
Attorney, Agent, or Firm—Oblon, Spivak, McClelland, Maier & Neustadt, P.C.

[57] ABSTRACT

A lighting device for an observation/image pickup apparatus capable of satisfactorily illuminating a surface of an observed section of a specimen sample for observation irrespective of whether a fine roughness is provided on the specimen surface. Illumination control slit members for laterally projected light, deflected oblique light, vertically projected light, and light composed of laterally projected light and vertically projected light, are provided, and selectively face an illumination light introducing section, to thereby convert illumination light (introduced through the illumination light introducing section) into any desired one of: laterally projected light, deflected oblique light, vertically projected light, and light composed of laterally projected light and vertically projected light, resulting in a surface of an observed section of a specimen sample being illuminated with the converted light.

14 Claims, 7 Drawing Sheets

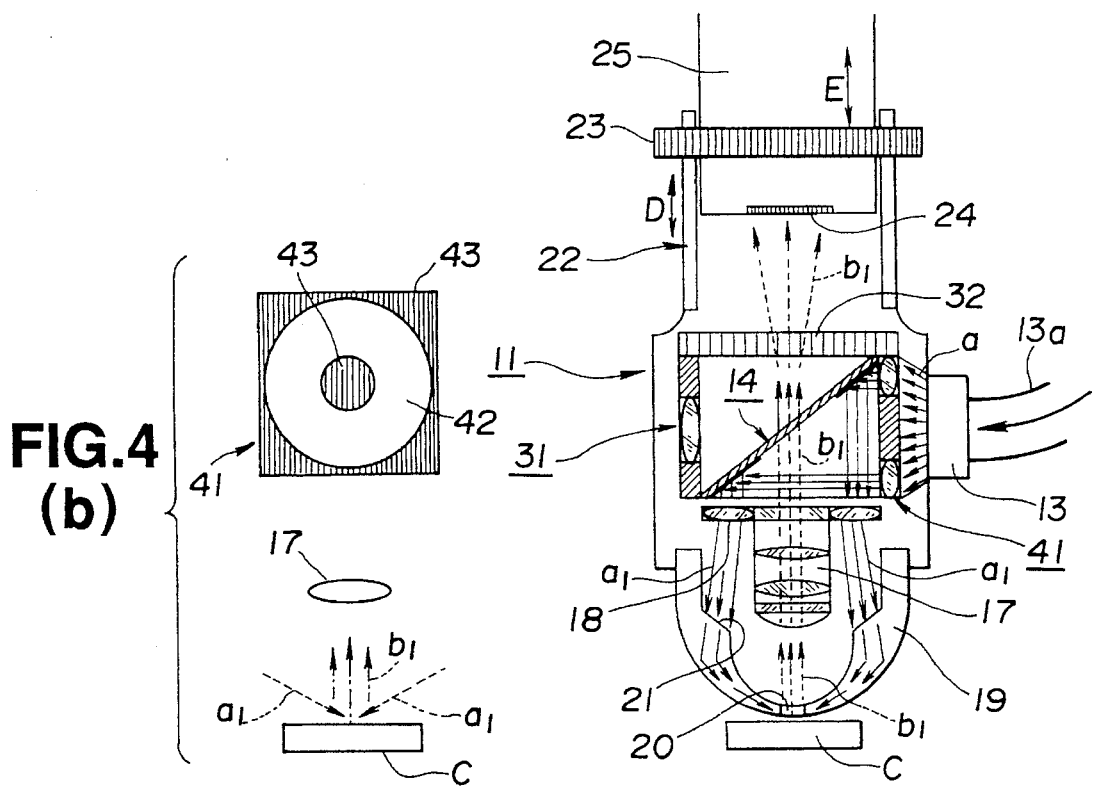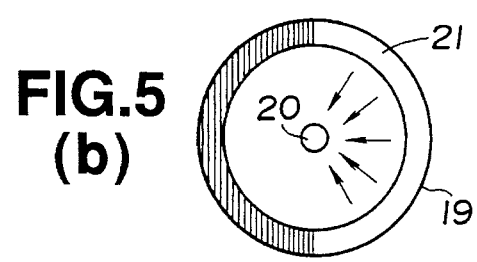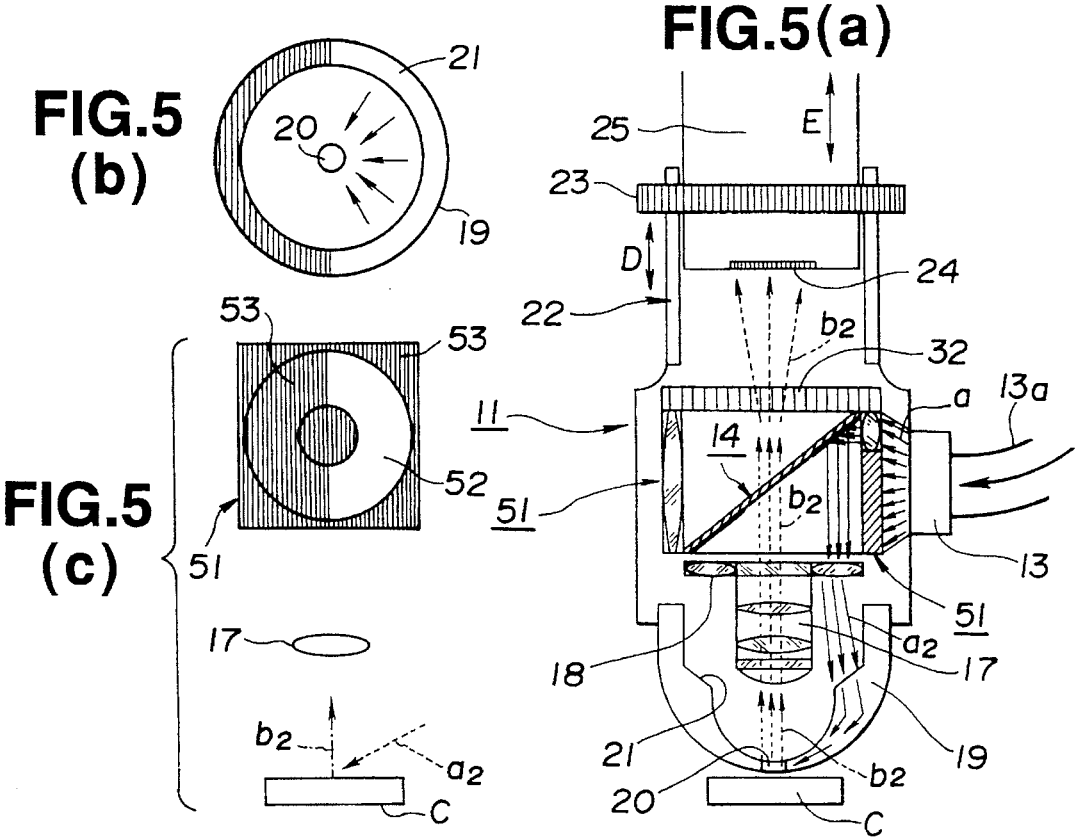

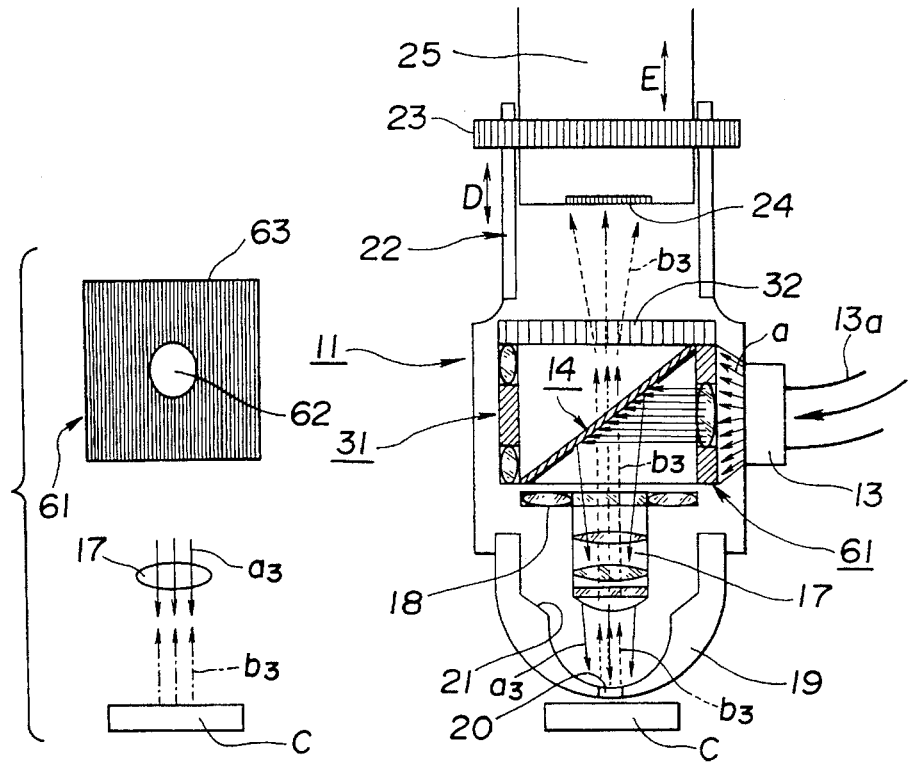
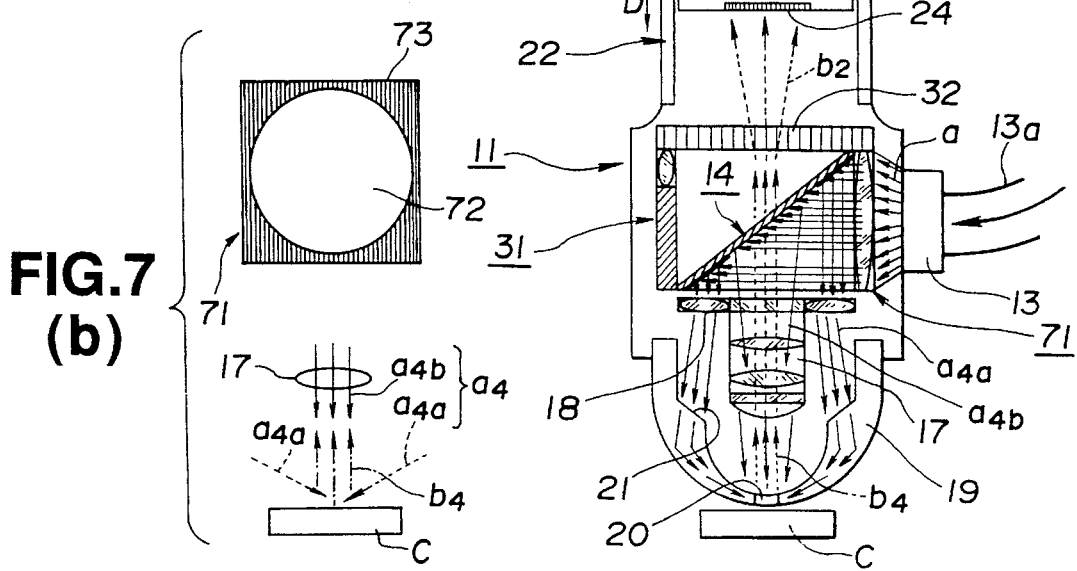

LIGHTING DEVICE FOR AN OBSERVATION/IMAGE PICKUP APPARATUS

BACKGROUND OF THE INVENTION

1. Field of the Invention

The invention relates to a lighting device for an observation/image pickup apparatus, and more particularly to a lighting device for an observation/image pickup apparatus for observing or picking up an image of a surface of a specimen sample.

In particular, the present invention relates to a lighting device for an observation/image pickup apparatus for lighting a surface of a section to be observed (hereinafter referred to as "observed section") of a specimen sample by means of laterally projected light, deflected oblique light, vertically projected light, or light composed of laterally projected light and vertically projected light as required, or by means of any one of laterally projected light and vertically projected light selected as desired.

2. Discussion of the Background

An observation apparatus and an image pickup apparatus which have been conventionally used in the art are each generally constructed such that a lighting head or an image pickup head, having a light projecting means for illumination incorporated therein, is arranged opposite to a surface of an observed section of a specimen sample to light an observed section and/or obtain an image or enlarged image of the surface thereof. An observation apparatus allows the direct observation of the image thus obtained, whereas the image pickup apparatus is adapted to display the image on an image surface of a TV monitor, to thereby indirectly observe the observed section. In each of the observation apparatus and the image pickup apparatus, illumination of the surface of the observed section of the specimen sample with light is carried out by illuminating the surface of the observed section with only oblique light, which is directed obliquely from a side surface of the observed section (or light mainly consisting of so-called laterally projected light), or light illuminating the observed section with only parallel rays directed vertically from a flat surface of the observed section opposite to the surface of the observed section (or light mainly consisting of so-called vertically projected light).

The lighting techniques using light primarily consisting of laterally projected light or the lighting techniques using light primarily consisting of vertically projected light, fail to permit the roughness to be precisely observed, particularly when a plane surface section of the specimen sample has a relatively fine roughness formed thereon. In order to eliminate this problem, it could be considered to combine both lighting techniques. Unfortunately, such a combination can render the apparatus quite complex.

SUMMARY OF THE INVENTION

The present invention has been made in view of the foregoing disadvantages of the prior art.

Accordingly, it is an object of the present invention to provide a lighting device for an observation/image pickup apparatus which is capable of permitting a surface of an observed section of a specimen sample to be satisfactorily illuminated for observation with any one of: laterally projected light in an entire circumferential direction, deflected oblique light in a partial circumferential direction, vertically projected light, and light composed of vertically projected light and laterally projected light selected as desired, irrespective of whether a relatively fine roughness is present on the surface of the observed section of the specimen sample, to thereby provide a lighted image of the surface which can be readily observed in the same visual field while maintaining a simplified structure for the device.

It is another object of the present invention to provide a lighting device for an observation/image pickup apparatus which is capable of permitting a surface of an observed section of a specimen sample to be satisfactorily illuminated for observation with laterally projected light in an entire circumferential direction, or vertically projected light, selected as desired irrespective of whether a relatively fine roughness is present on the surface of the observed section of the specimen sample, to thereby provide a lighted image of the surface which can be readily observed in the same visual field while maintaining a simplified structure for the device.

In accordance with the present invention, a lighting device for an observation/image pickup apparatus is provided. The lighting device includes a lens tube including a cylindrical barrel provided on one side of an outer periphery thereof, with an illumination light introducing section which permits illumination light to be introduced therethrough into the lens tube. The cylindrical barrel is provided therein with a half mirror member which faces the illumination light introducing section at a predetermined angle on a central optical axis. The half mirror member includes, on a peripheral portion thereof, an annular mirror section. The half mirror member further includes, at a central portion thereof, a half mirror section. The lens tube is provided therein with an illumination switching cylinder which is rotatable and which surrounds the half mirror member about the central optical axis. The lighting device also includes an image pickup optical system arranged below the half mirror member, including an objective lens arranged so as to positionally correspond to the half mirror section along the central optical axis, an annular converging lens arranged below the half mirror member and positionally corresponding to the annular mirror section, and a converging guide member arranged below the image pickup optical system and annular converging lens in a manner to positionally correspond to the annular converging lens. The converging guide member includes an objective opening facing a surface of an observed section of a specimen sample on the central optical axis. Further, the illumination switching cylinder is provided, on a periphery thereof, with a plurality of illumination control slit members which respectively permit the illumination light introduced into the lens tube through the illumination light introducing section to be selectively converted into at least: laterally projected light, deflected oblique light, vertically projected light, and light composed of laterally projected light and vertically projected light. The illumination control slit members are arranged so that any one thereof selectively faces the illumination light introducing section as desired.

Thus, in the lighting device of the present invention, any one of the illumination control slit members for laterally projected light, deflected oblique light, vertically projected light, and light composed of laterally projected light and vertically projected light is permitted to selectively face the illumination light introducing section, to thereby convert the illumination light introduced into the illumination light introducing section into any desired one of laterally projected light, deflected oblique light, vertically projected light, and light composed of laterally projected light and vertically projected light, resulting in the surface of the observed section of the specimen sample being illuminated with the converted light.

When the illumination control slit member for laterally projected light faces the illumination light introducing section, illumination light introduced into the illumination light introducing section is converted into laterally projected light through the illumination control slit member, so that the surface of the observed section of the specimen sample may be independently illuminated with the light in an entire circumferential direction or section.

When the illumination control slit member for deflected oblique light faces the illumination light introducing section, illumination light introduced into the illumination light introducing section is converted into deflected oblique light in a semi-circumferential section through the illumination control slit member, so that the surface of the observed section of the specimen sample may be independently illuminated with the light in a semi-circumferential direction or section.

When the illumination control slit member for vertically projected light faces the illumination light introducing section, illumination light introduced into the illumination light introducing section is converted into corresponding vertically projected light through the illumination control slit member, so that the surface of the observed section of the specimen sample may be independently illuminated with the light in a vertical direction.

When the illumination control slit member for light composed of laterally projected light and vertically projected light is permitted to face the illumination light introducing section, illumination light introduced into the illumination light introducing section is converted into corresponding laterally projected light in an entire circumferential direction and vertically projected light in a vertical direction through the illumination control slit member, so that the surface of the observed section of the specimen sample may be independently illuminated in a direction composed of both light in an entire circumferential direction and light in a vertical direction.

In accordance with one aspect of a preferred embodiment of the present invention, the illumination control slit members each include a focusing optical system for rendering rays of illumination light introduced through the illumination light introducing section parallel to each other. This construction permits rays of each of the selected laterally projected light, deflected oblique light, vertically projected light, and composed light, to be rendered parallel, so that the surface of the observed section of the specimen sample may be more effectively illuminated.

In accordance with another aspect of a preferred embodiment of the present invention, the illumination control slit member for laterally projected light is provided at only a portion thereof corresponding to the annular mirror section with a focusing lens acting as a light permeable section. This construction permits rays of illumination light introduced into the illumination light introducing section to pass through the focusing lens of the illumination control slit member for laterally projected light, resulting in the light rays being parallel to each other, so that laterally projected light exhibiting directionality desired for illumination light may be readily obtained.

In accordance with a further aspect of a preferred embodiment of the present invention, the illumination control slit member for deflected oblique light is provided at only a portion thereof corresponding to a part of the annular mirror section with a focusing lens acting as a light permeable section. This construction permits rays of illumination light introduced into the illumination light introducing section to pass through the focusing lens of the illumination control slit member for deflected oblique light, to provide partially corresponding parallel rays, so that deflected oblique light exhibiting directionality desired for illumination light may be readily obtained.

In accordance with another aspect of a preferred embodiment of the present invention, the illumination control slit member for vertically projected light is provided at only a portion thereof corresponding to a part of the half mirror section, with a focusing lens acting as a light permeable section. This construction permits rays of illumination light introduced into the illumination light introducing section to pass through the focusing lens of the illumination control slit member for vertically projected light, resulting in the light rays being rendered parallel to each other, so that vertically projected light exhibiting directionality desired for illumination light may be readily obtained.

In a preferred embodiment of the present invention, the illumination control slit member for light composed of laterally projected light and vertically projected light is provided at only a portion thereof corresponding to each of the annular mirror section and the half mirror section, with a focusing lens acting as a light permeable section. This construction permits rays of illumination light introduced into the illumination light introducing section to pass through the focusing lens of the illumination control slit member for the composed light corresponding to each of the annular mirror section and half mirror section, resulting in the light ray being rendered parallel to each other, so that light composed of laterally projected light and vertically projected light each exhibiting directionality desired for illumination light may be readily obtained.

Also, in accordance with the present invention, a lighting device for an observation/image pickup apparatus is provided. The lighting device includes a lens tube including a cylindrical barrel provided on one side of an outer periphery thereof with an illumination light introducing section which permits illumination light to be introduced therethrough into the lens tube. The cylindrical barrel is provided therein with a half mirror member which faces the illumination light introducing section at a predetermined angle on a central optical axis. The half mirror member is formed on a peripheral portion thereof with an annular mirror section and at a central portion thereof with a half mirror section. The lens tube is provided with an illumination switching cylinder which is rotatable and which surrounds the half mirror member about the central optical axis. The lighting device also includes an image pickup optical system arranged below the half mirror member, including an objective lens arranged so as to positionally correspond to the half mirror section on the central optical axis, an annular converging lens arranged below the half mirror member and positionally correspond to the annular mirror section, and a converging guide member arranged below the image pickup optical system and annular converging lens in a manner to positionally correspond to the annular converging lens. The converging guide member is formed with an objective opening facing a surface of an observed section of a specimen sample on the central optical axis. The illumination switching cylinder is provided, on a periphery thereof, with a plurality of illumination control slit members for respectively permitting illumination light introduced into the lens tube through the illumination light introducing section to be converted into at least: laterally projected light, deflected oblique light, vertically projected light, and light composed of laterally projected light and vertically projected light. The illumination control slit member for deflected oblique light is rotatably arranged to be perpendicular to an incident optical axis of the illumination light introducing section. The illumination control slit members are so arranged that any one thereof can selectively face the illumination light introducing section as desired, so that lighting of the specimen sample by each of laterally projected light, deflected oblique light, vertically projected light, and light composed of laterally projected light and vertically projected light may be carried out; and when the illumination control slit member for deflected oblique light is selected, the illumination control slit member for deflected oblique light is selectively rotated on or about the incident optical axis of the illumination light introducing section to set an angle of deflected oblique light with respect to the specimen sample as desired.

In the lighting device of the present invention thus constructed, any one of the illumination control slit members for laterally projected light, deflected oblique light, vertically projected light, and light composed of laterally projected light and vertically projected light is permitted to selectively face the illumination light introducing section, to thereby convert illumination light introduced into the illumination light introducing section into any desired one of laterally projected light, deflected oblique light, vertically projected light, and light composed of laterally projected light and vertically projected light, resulting in the surface of the observed section of the specimen sample being illuminated with the converted light. Also, when the illumination control slit member for deflected oblique light is permitted to selectively face the illumination light introducing section, the illumination control slit member may be rotated to vary an angular range of illumination by deflected oblique light.

When the illumination control slit member for laterally projected light is permitted to face the illumination light introducing section, illumination light introduced into the illumination light introducing section is converted into laterally projected light through the illumination control slit member, so that the surface of the observed section of the specimen sample may be independently illuminated with the light in an entire circumferential direction When the illumination control slit member for deflected oblique light is permitted to face the illumination light introducing section, illumination light introduced into the illumination light introducing section is converted into deflected oblique light in a semi-circumferential direction through the illumination control slit member, so that the surface of the observed section of the specimen sample may be independently illuminated with the light in a semi-circumferential direction.

When the illumination control slit member for vertically projected light is permitted to face the illumination light introducing section, illumination light introduced into the illumination light introducing section is converted into corresponding vertically projected light through the illumination control slit member, so that the surface of the observed section of the specimen sample may be independently illuminated with the light in a vertical direction.

When the illumination control slit member for light composed of laterally projected light and vertically projected light is permitted to face the illumination light introducing section, illumination light introduced into the illumination light introducing section is converted into corresponding laterally projected light in an entire circumferential direction and vertically projected light in a vertical direction through the illumination control slit member, so that the surface of the observed section of the specimen sample may be independently illuminated in a direction composed of both light in an entire circumferential direction and light in a vertical direction.

Further, in accordance with the present invention, an alternate lighting device for an observation/image pickup apparatus is provided. The lighting device includes a lens tube including a cylindrical barrel provided on one side of an outer periphery thereof, with an illumination light introducing section which permits illumination light to be introduced into the lens tube. The cylindrical barrel is provided with a half mirror member which faces the illumination light introducing section at a predetermined angle on a central optical axis. The half mirror member includes, on a peripheral portion thereof, an annular mirror section. In addition, the half mirror member includes, at a central portion thereof, a half mirror section. The lighting device also includes an observation optical system arranged below the half mirror member, including an objective lens arranged so as to positionally correspond to the half mirror section on the central optical axis and a converging guide member, including an outside optical path, an inside optical path and an optical path switching damper arranged on an upper light-guide side of the half mirror member opposite to the annular mirror section for carrying out switching between the downwardly extending outside optical path and the inside optical path. The outside optical path is provided with an objective opening facing a surface of an observed section of a specimen sample and the inside optical path is provided with a lower opening directed toward the specimen sample. The optical path switching damper is switched toward the inside optical path to permit illumination light introduced into the outside optical path to be applied in the form of laterally projected light from an inner periphery of the objective opening to the specimen sample. The optical path switching damper is switched toward the outside optical path to permit illumination light introduced into the inside optical path to be applied in the form of vertically projected light from the lower opening to the specimen sample. In the lighting device of the present invention thus constructed, switching of the optical path switching damper toward the inside optical path permits illumination light introduced into the outside optical path to be converted into laterally projected light for illuminating the surface of the observed section of the specimen sample. In addition, switching of the optical path switching damper toward the outside optical path permits illumination light introduced into the inside optical path to be converted into vertically projected light for illuminating the surface of the observed section of the specimen sample.

BRIEF DESCRIPTION OF THE DRAWINGS

These and other objects and many of the attendant advantages of the present invention will be readily appreciated as the same becomes better understood by reference to the following detailed description, particularly when considered in conjunction with the accompanying drawings, wherein:

FIGS. 3(a) to 3(d) each show a built-in type illumination control slit member of the focusing optical system incorporated in the illumination switching cylinder shown in FIG. 2, wherein FIG. 3(a) is a front elevation (or plan) view showing an illumination control slit member for laterally projected light, FIG. 3(b) is a front elevation view showing an illumination control slit member for deflected oblique light, FIG. 3(c) is a front elevation view showing an illumination control slit member for vertically projected light, and FIG. 3(d) is a front elevation view showing an illumination control slit member for light composed of laterally projected light and vertically projected light;

FIG. 4(a) is a vertical sectional view showing an optical path of each of the illumination light and the image pickup light obtained when lighting by laterally projected light is applied to the image pickup apparatus of FIG. 1;

FIG. 4(b) is a schematic view showing the relationship between a slit member for laterally projected light and each of the illumination light and the image pickup light with respect to a specimen sample;

FIG. 5(a) is a vertical sectional view showing an optical path of each of the illumination light and the image pickup light obtained when lighting by deflected oblique light is applied to the image pickup apparatus of FIG. 1;

FIG. 5(b) is a schematic view showing an illumination range of the illumination light by a deflected oblique light slit member in lighting shown in FIG. 5(a);

FIG. 5(c) is a schematic view showing the relationship between a slit member for deflected oblique light and each of the illumination light and the image pickup light with respect to a specimen sample;

FIG. 6(a) is a vertical sectional view showing an optical path of each of the illumination light and the image pickup light obtained when lighting by vertically projected light is applied to the image pickup apparatus of FIG. 1;

FIG. 6(b) is a schematic view showing the relationship between a slit member for vertically projected light and each of the illumination light and the image pickup light with respect to a specimen sample;

FIG. 7(a) is a vertical sectional view showing an optical path of each of the illumination light and the image pickup light obtained when lighting by light composed of laterally projected light and vertically projected light is applied to the image pickup apparatus of FIG. 1;

FIG. 7(b) is a schematic view showing the relationship between a slit member for light composed of laterally projected light and vertically projected light and each of the illumination light and the image pickup light with respect to a specimen sample;

FIGS. 10(a) to 10(d) each show a built-in type illumination control slit member of the focusing optical system incorporated in the illumination switching cylinder shown in FIG. 9, wherein FIG. 10(a) is a front elevation view showing an illumination control slit member for laterally projected light, FIG. 10(b) is a front elevation view showing an illumination control slit member for deflected oblique light, FIG. 10(c) is a front elevation view showing an illumination control slit member for vertically projected light, and FIG. 10(d) is a front elevation view showing an illumination control slit member for light composed of laterally projected light and vertically projected light;

DETAILED DESCRIPTION OF THE PREFERRED EMBODIMENTS

Figure 8:
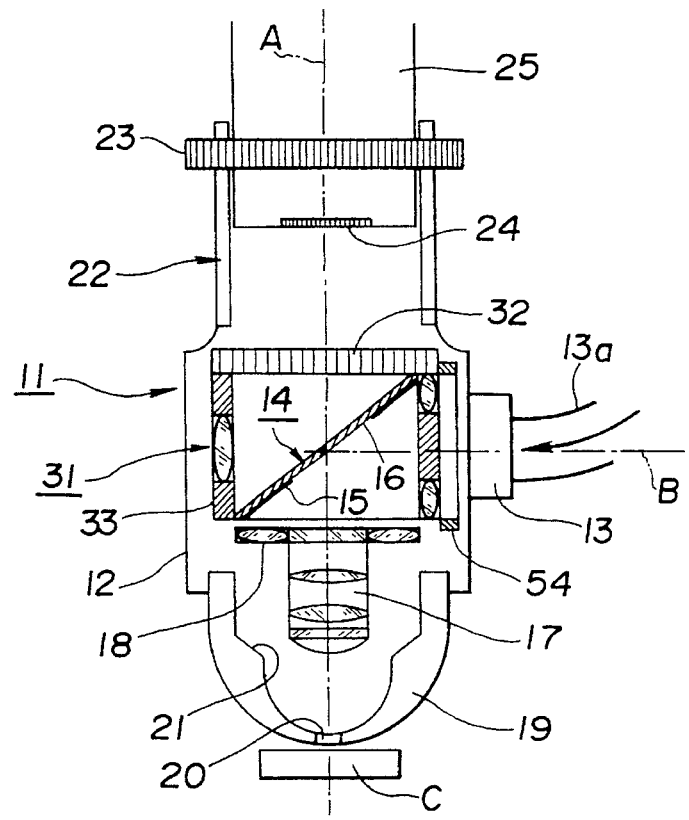
FIG. 8 is a vertical sectional view schematically showing an image pickup apparatus to which a second embodiment of a lighting device according to the present invention is applied.
Figure 9:
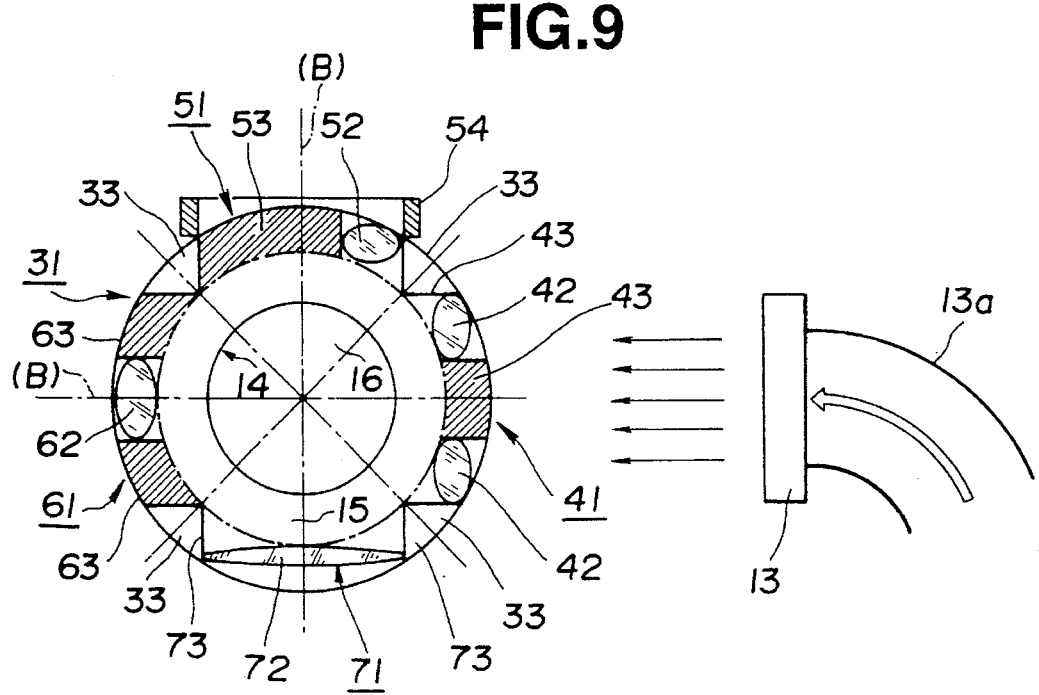
FIG. 9 is an enlarged cross sectional view schematically showing an illumination switching cylinder incorporated in the lighting device of FIG. 8.
Figure 11:
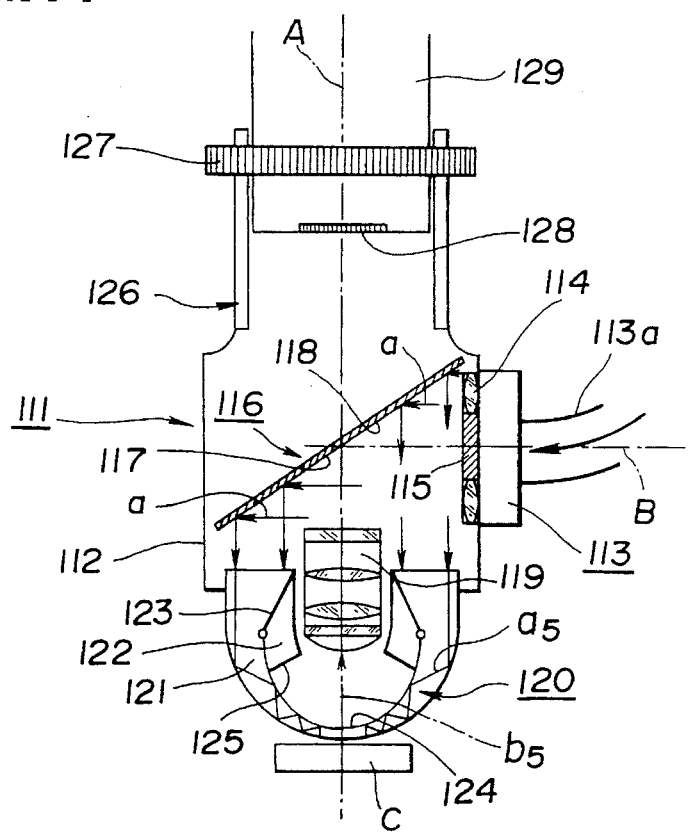
FIG. 11 is a vertical sectional view schematically showing an image pickup apparatus on which lighting by laterally projected light is applied according to a third embodiment of a lighting device of the present invention.
Figure 12:
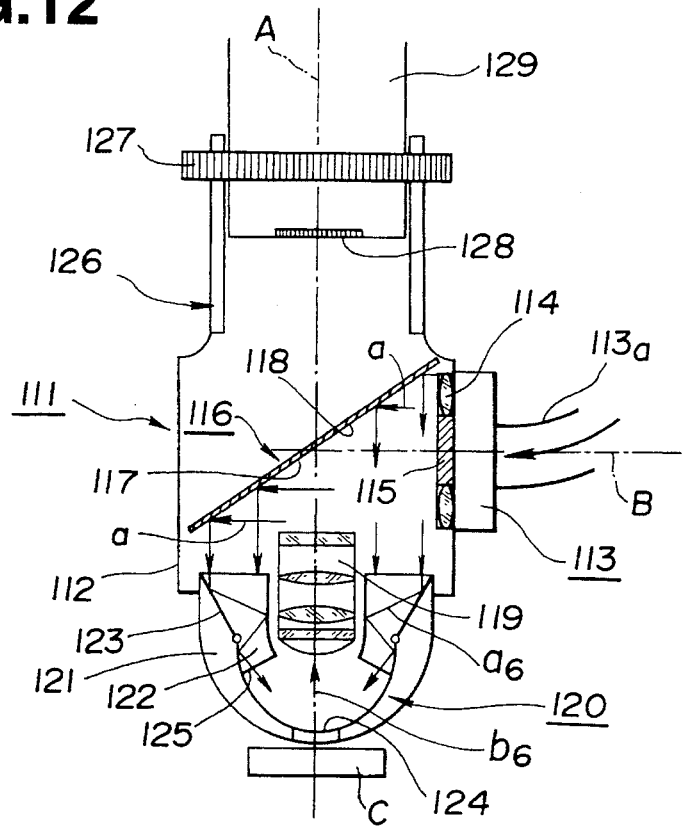
FIG. 12 is a vertical sectional view schematically showing the image pickup device of FIG. 11 on which lighting by vertically projected light is applied means of the light device of FIG. 11.

A lighting device for an observation/image pickup apparatus according to the present invention will now be described hereinafter with reference to the accompanying drawings in which FIGS. 1 to 3, as well as FIGS. 4 to 7, show a first embodiment of a lighting device for an observation/image pickup apparatus according to the present invention. FIGS. 8 to 10 show a second embodiment of a lighting device for an observation/image pickup apparatus according to the present invention, and FIGS. 11 and 12 show a third embodiment of a lighting device for an observation/image pickup apparatus according to the present invention.

A lighting device of each of the illustrated embodiments is applied to an image pickup apparatus, however, it is to be understood that the present invention is likewise applicable to an observation apparatus, i.e., for directly observing the illuminated specimen.

First, the first embodiment of the present invention shown in FIGS. 1 to 3 will be described while concurrently secondarily describing the second embodiment shown in FIGS. 8 to 10 (which respectively correspond to FIGS. 1 to 3).

Figure 1:
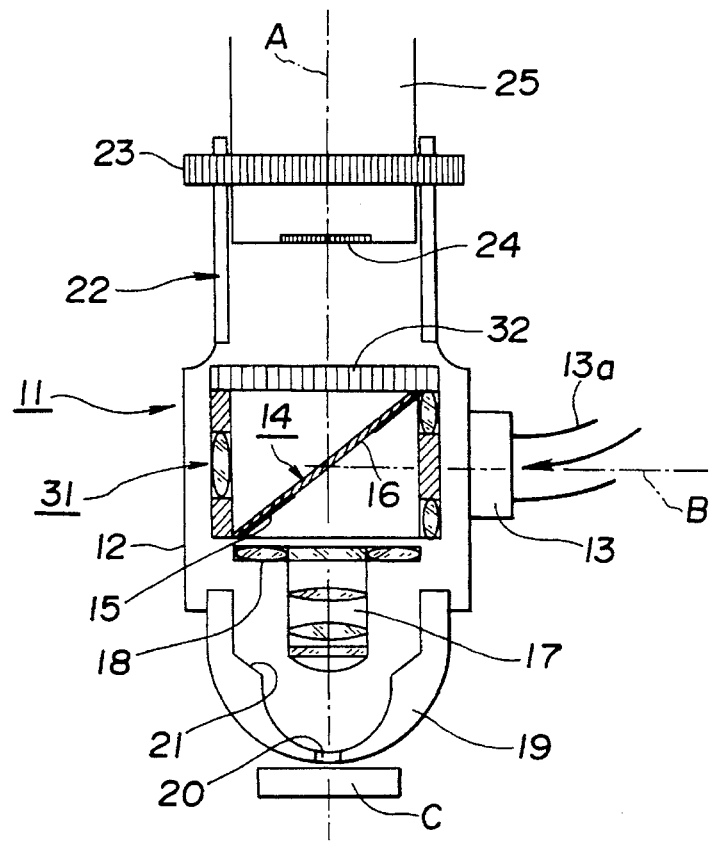
FIG. 1 is a vertical sectional view schematically showing an image pickup apparatus to which a first embodiment of a lighting device according to the present invention is applied.

FIG. 1 is a vertical sectional view schematically showing an image pickup apparatus according to the first embodiment of the lighting device according to the present invention. FIG. 2 is an enlarged cross sectional view schematically showing an illumination switching cylinder incorporated in the lighting device of FIG. 1.

Figure 2:
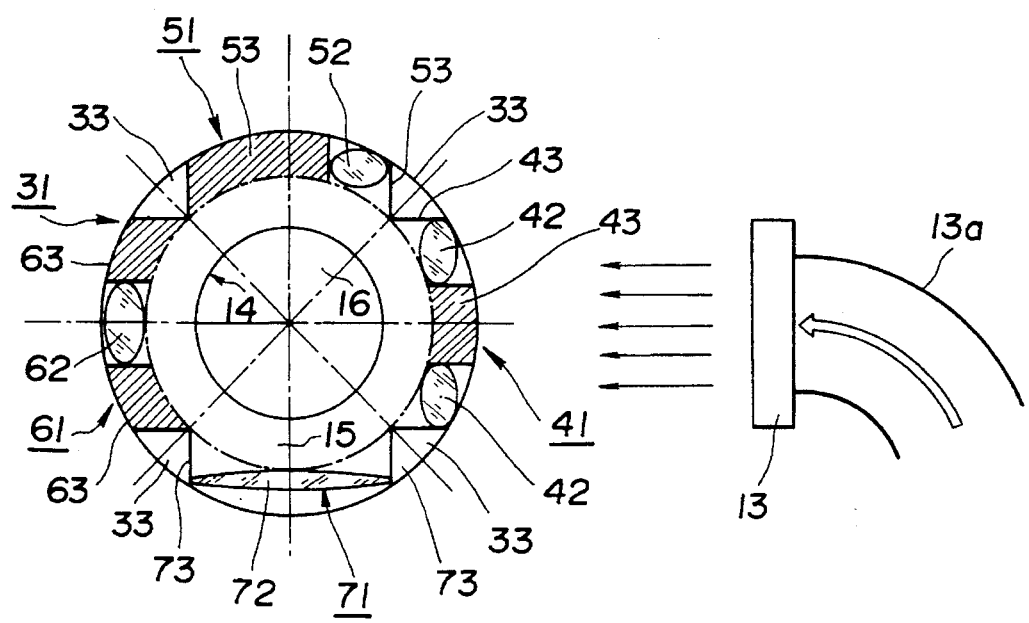
FIG. 2 is an enlarged cross sectional view schematically showing an illumination switching cylinder incorporated in the lighting device of FIG. 1.
Figure 3A:
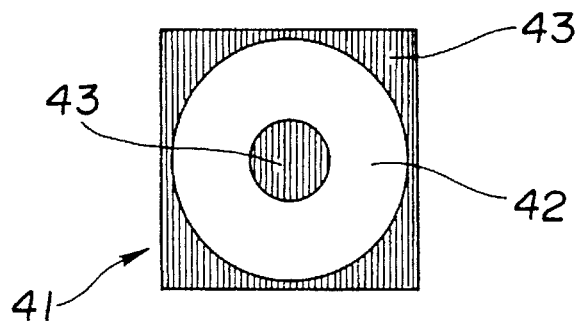
Figure 3B:
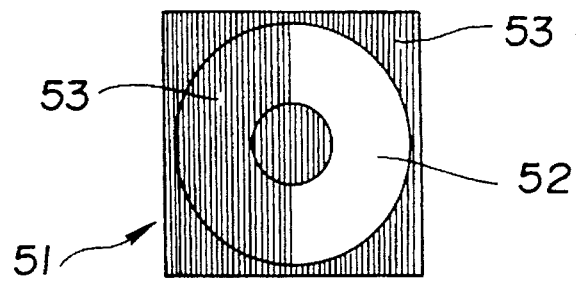
Figure 3C:
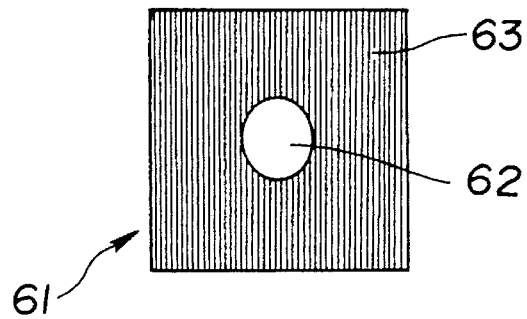
Figure 3D:
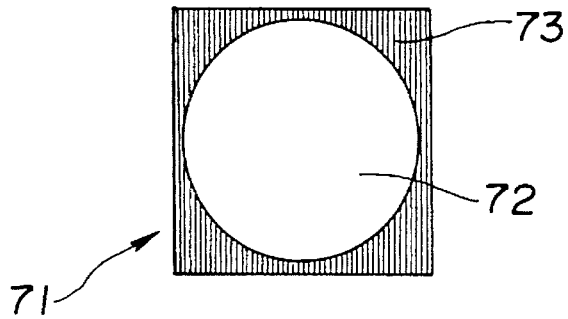

FIGS. 3(a) to 3(d) each show a built-in illumination control slit member of the focusing optical system incorporated in the illumination switching cylinder shown in FIG. 2, wherein FIG. 3(a) is a front elevation view showing an illumination control slit member for laterally projected light (hereinafter referred to as "laterally projected light slit member"). FIG. 3(b) is a front elevation view showing an illumination control slit member for deflected oblique light (hereinafter referred to as "deflected oblique light slit member"). FIG. 3(c) is a front elevation view showing an illumination control slit member for vertically projected light (hereinafter referred to as "vertically projected light slit member"). In addition, FIG. 3(d) is a front elevation view showing an illumination control slit member for light composed of laterally projected light and vertically projected light (hereinafter referred to as "composed light slit member").

FIGS. 8 and 9 are a vertical sectional view and an enlarged cross sectional view showing the second embodiment of the lighting device of the present invention, which respectively correspond to FIGS. 1 and 2. FIGS. 10(a) to 10(d), also show the second embodiment, and respectively correspond to FIGS. 3(a) to 3(d).

In each of the first embodiment shown in FIGS. 1 to 3, and the second embodiment shown in FIGS. 8 to 10, the image pickup apparatus includes a lens tube 11, which is provided with a cylindrical barrel 12. The cylindrical barrel 12 is provided, on a part or one side of an outer periphery thereof, with an illumination light introducing section 13 which permits illumination light on an incident optical axis B transmitted through an optical fiber bundle 13a to be introduced therethrough into the lens tube 11. The cylindrical barrel 12 is provided therein with a half mirror member 14. The half mirror member 14 faces the illumination light introducing section 13 while being kept oblique at an angle of 45 degrees on a central optical axis A. The half mirror member 14 includes, on a peripheral portion of a lower side (i.e., the downwardly facing surface) thereof, with an annular mirror section 15 and on a central portion thereof with a half mirror section 16. The annular mirror section 15 is separately formed on the half mirror member 14 by deposition. Also, the lens tube 11 includes an illumination switching cylinder 31 arranged around the half mirror member 14 in the cylindrical barrel 12 so as to surround the half mirror member 14. The illumination switching cylinder 31 is provided with a switching operation ring 32, and rotates about the central optical axis A, as described in detail hereinafter.

The lens tube 11 is provided therein with an image pickup optical system 17 which is arranged below the half mirror member 14 and which includes an objective lens arranged so as to positionally correspond to the half mirror section 16 of the half mirror member 14 along the central optical axis A. In addition, the lens tube 11 is provided therein with an annular converging lens 18, which is arranged so as to define an outer peripheral section of the image pickup optical system 17, and to positionally correspond to the annular mirror section 15. The lens tube 11 includes a converging guide member 19 connected to or mounted on a lower portion of the cylindrical barrel 12 in a manner to be positioned below the image pickup optical system 17 and below annular converging lens 18, and so as to at least partially surround the image pickup optical system 17. The converging guide member 19 includes an objective opening 20 which faces a surface of an observed section of a specimen sample C, and which is provided on an inner peripheral surface thereof with an annular converging step 21 so as to positionally correspond to the annular converging lens 18.

The lens tube 11 also includes a focus mechanism 22 arranged on the cylindrical barrel 12 so as to constitute an upper section of the lens tube 11, which focus mechanism 22 may be constructed in a manner conventionally known in the art. The focus mechanism 22 is adapted to be actuated for focusing by means of a focus operation ring 23. The focus mechanism 22 is provided therein with a CCD element 24, which is arranged so as to be positioned on the central optical axis A, and includes a variable magnifying mechanism 25 which may be constructed in a manner conventionally known in the art.

The illumination switching cylinder 31, equipped with the switching operation ring 32, as shown in FIGS. 2 and 3(a) to 3(d) or FIGS. 9 and 10(a) to 10(d), includes a holding cylinder 33 arranged so as to be rotated about the central optical axis A and around the half mirror member 14 by means of the switching operation ring 32. In the illustrated embodiment, it is that the holding cylinder 33 is preferably rotated intermittently by 90 degrees (i.e., the slit members are at 90 degree intervals). The holding cylinder 33 is divided into four sections at angular intervals of 90 degrees in a circumferential direction thereof, in which a laterally projected light slit member 41, a deflected oblique light slit member 51, a vertically projected light slit member 61 and a composed light slit member 71 are fitted, respectively. The slit members 41, 51, 61 and 71 each have a focusing optical system incorporated therein for permitting rays of illumination light introduced therein through the illumination light introducing section 13 to be parallel to each other. A selective switching operation of the switching operation ring 32 permits the slit members 41, 51, 61 and 71 to selectively alternately face the illumination light introducing section 13.

Figure 10A:
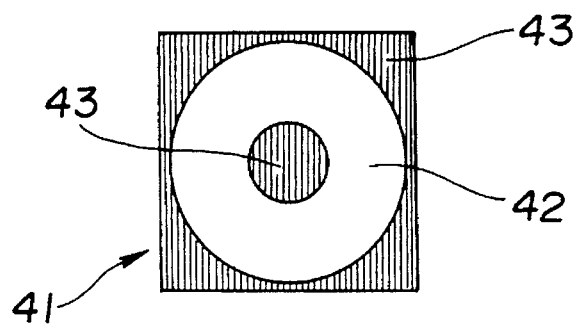

The laterally projected light slit member 41, as shown in FIG. 3(a) or 10(a), is provided (at a portion thereof corresponding to an entire circumference of the annular mirror section 15 of the half mirror member 14) with a focusing lens 42 of an annular shape for focusing illumination light, so that the annular focusing lens 42 acts as a light permeable section of the slit member 41, while the remaining part of the slit member 41 is a light non-permeable section 43.

Figure 10B:
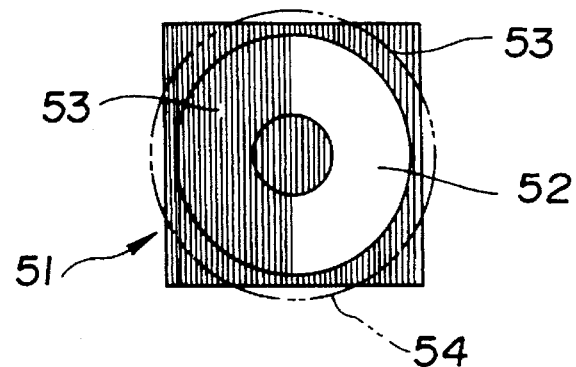

The deflected oblique light slit member 51, as shown in FIG. 3(b) or 10(b), is provided (at a portion thereof corresponding to a part of a circumference of the annular mirror section 15 of the half mirror member 14) with a focusing lens 52 having a semi-annular shape for focusing illumination light, so that the focusing lens 52 acts as a light permeable section of the slit member 51, while the remaining part of the slit member 51 is a light non-permeable section 53. In each of the first and second embodiments, the focusing lens 52 is arranged so as to positionally correspond to a right-hand half of the annular mirror section 15. Also, in the second embodiment, as shown in FIG. 10(b), a rotation operation ring 54 is provided for rotating the focusing lens 52 about the incident optical axis B as desired.

Figure 10C:
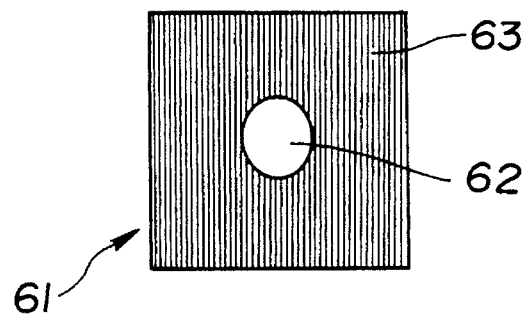

The vertically projected light slit member 61, as shown in FIG. 3(c) or 10(c), is provided at a portion thereof corresponding to the half mirror section 16 of the half mirror member 14 with a focusing lens 62 for focusing illumination light, so that the focusing lens 62 acts as a light permeable section, while the remaining part of the slit member 61 is a light non-permeable section 63.

Figure 10D:
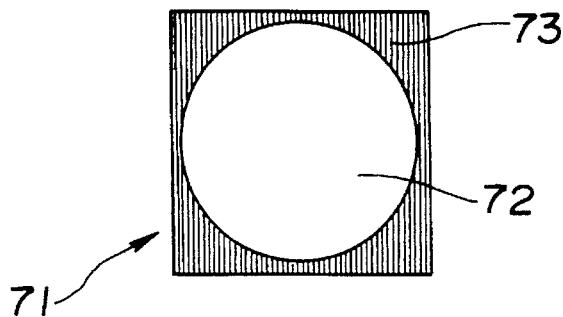

The composed light slit member 71, as shown in FIGS. 3(d) or 10(d), is provided at a portion thereof corresponding to an entire circumference of each of the annular mirror section 15 and half mirror section 16 of the half mirror member 14 with a focusing lens 72 for focusing illumination light, so that the focusing lens 72 acts as a light permeable section, while the remaining part of the slit member 71 is a light non-permeable section 73.

Now, the manner of operation of each of the first and second embodiments constructed as described above will be described hereinafter with reference to FIGS. 4 to 7.

The following description will be made on the assumption that a specimen sample C, arranged so as to face the objective opening 20 of the lens tube 11, has been subjected to a focusing operation (in the direction represented by arrow D) by the focus mechanism 22 utilizing the focus operation ring 23, as well as a magnification varying operation E by the variable magnification mechanism 25 in each of the illumination modes, and the image pickup light b obtained by lighting the specimen sample c in each of the illumination modes is set so as to properly enter the CCD element 24.

FIG. 4(a) is a vertical sectional view showing an optical path of each of the illumination light and the image pickup light obtained when a lighting mode provided by laterally projected light (hereinafter referred to as "first lighting mode" or "first illumination mode") is applied to the image pickup apparatus of the first embodiment. FIG. 4(b) is a schematic view showing the relationship between the laterally projected light slit member selected for the first lighting mode and each of the illumination light and the image pickup light with respect to the specimen sample.

The first lighting mode, as shown in FIGS. 4(a) and 4(b), is carried out by a selective switching operation of the switching operation ring 32 so that the laterally projected light slit member 41 of the illumination switching cylinder 31 faces the illumination light introducing section 13.

More particularly, in the first lighting mode, rays of illumination light (a), introduced into the illumination light introducing section 13, are permitted to pass through only the focusing lens 42 being annular of the laterally projected light slit member 41, resulting in the light rays being rendered parallel to each other. The light is then reflected by the annular mirror section 15 formed on the entire periphery of the half mirror member 14, to thereby be downwardly directed, in the direction of the central optical axis A. Then, the rays are permitted to pass through the annular converging lens 18 and are introduced from the annular converging step 21 into the converging guide member 19, to thereby provide laterally projected light discharged in an entire or full circumferential direction from the objective opening 20, so that an observed section of the specimen sample C is illuminated with the light $a_1$. Thus, the observed section of the specimen sample C is independently illuminated with the laterally projected light $a_1$ in the entire or full circumferential direction.

The image pickup light $b_1$ reflected by the observed section of the specimen sample C is guided from the objective opening 20 through the image pickup optical system 17 to the half mirror section 16 of the half mirror member 14, with the light then introduced into the CCD element 24. The CCD element 24 converts the image pickup light $b_1$ into an electrical signal, which is then displayed on an image plane of a TV monitor (not shown). This provides an image of the observed section of the specimen sample C illuminated with the laterally projected light $a_1$ as desired, or the image illuminated in the first lighting made is readily and effectively observed.

FIG. 5(a) is a vertical sectional view showing an optical path of each of the illumination light, and the image pickup light obtained when a lighting mode provided by deflected oblique light (hereinafter referred to as "second lighting mode" or "second illumination mode") is applied to the image pickup apparatus of the first embodiment. FIG. 5(b) is a schematic view showing an illumination range of the illumination light by a deflected oblique light slit member selected for the second lighting mode shown in FIG. 5(a), and FIG. 5(c) is a schematic view showing the relationship between the deflected oblique light slit member selected for the second lighting mode and each of the illumination light and the image pickup light with respect to the specimen sample.

The second lighting mode, as shown in FIGS. 5(a) to 5(c), is carried out by a selective switching operation of the switching operation ring 32 so that the deflected oblique light slit member 51 of the illumination switching cylinder 31 faces the illumination light introducing section 13.

More particularly, in the second lighting mode, rays of illumination light (a), introduced into the illumination light introducing section 13, are permitted to pass through only the focusing lens 52 being semi-annular, corresponding to the right-hand half of the deflected oblique light slit member 51, resulting in the light rays being parallel to each other. The light is then reflected by the right-hand half of the annular mirror section 15 of the half mirror member 14, to thereby be downwardly directed, in the direction of central optical axis A. The rays are then permitted to pass through the right-hand half of the annular converging lens 18, and are introduced from the annular converging step 21 into the converging guide member 19, to thereby provide deflected oblique light $a_2$ extending over a semicircumference on a right-hand half of the objective opening 20 or from the right-hand half of the objective opening 20. As a result, the observed section of the specimen sample C is independently illuminated with the deflected oblique light $a_2$ in a semicircumferential or right-hand half direction.

The image pickup light $b_2$ reflected by the observed section of the specimen sample C is likewise guided from the objective opening 20 through the image pickup optical system 17 to the half mirror section 16 of the half mirror member 14, with the light then introduced into the CCD element 24. The CCD element 24 converts the image pickup light $b_2$ into an electrical signal, which is then displayed on a TV monitor (not shown). This provides an image of the observed section of the specimen sample C illuminated with the deflected oblique light $a_2$ as desired, or the image illuminated in the second lighting modes is readily and effectively observed.

With regard to the second lighting mode, lighting of the image pickup apparatus of the second embodiment is carried out in a way different from that of the first embodiment, due to the arrangement of the rotation operation ring 54 (FIG. 10b). More particularly, a selective rotation operation of the rotation operation ring 54, as desired, permits an angular range of illumination or lighting by the deflected oblique light $a_2$ to be varied about the central optical axis A for observation.

FIG. 6(a) is a vertical sectional view showing an optical path of each of the illumination light and the image pickup light obtained when a lighting mode provided by vertically projected light (hereinafter referred to as "third lighting mode" or "third illumination mode") is applied to the image pickup apparatus of FIG. 1. FIG. 6(b) is a schematic view showing the relationship between the vertically projected light slit member selected for the third lighting mode and each of the illumination light and the image pickup light with respect to the specimen sample.

The third lighting mode, as shown in FIGS. 6(a) and 6(b), is carried out by a selective switching operation of the switching operation ring 32, such that the vertically projected light slit member 61 of the illumination switching cylinder 31 faces the illumination light introducing section 13.

More particularly, in the third lighting mode, rays of illumination light (a), introduced into the illumination light introducing section 13, are permitted to pass through only the focusing lens 62 formed at the central portion of the vertically projected light slit member 61, resulting in the light rays being the light rays parallel to each other. The light is then reflected by the half mirror section 16 of the half mirror member 14, to thereby be downwardly directed, in the direction of the central optical axis A. Then, the rays are permitted to pass through the image pickup optical system 17, to thereby provide vertically projected light $a_3$ from the objective opening 20, so that the observed section of the specimen sample C is illuminated with the light $a_3$. Thus, the observed section of the specimen sample C is independently illuminated with the laterally projected light $a_3$, projected in a vertical direction.

Then, image pickup light $b_3$ reflected by the observed section of the specimen sample C is guided from the objective opening 20 through the image pickup optical system 17 to the half mirror section 16 of the half mirror member 14 and then introduced into the CCD element 24. The CCD element 24 converts the image pickup light $b_3$ into an electrical signal, which is then displayed on a TV monitor (not shown). This provides an image of the observed section of the specimen sample C illuminated with the vertically projected light $a_3$ as desired, or the image illuminated in the third lighting mode is readily and effectively observed.

FIG. 7(a) is a vertical sectional view schematically showing an optical path of each of the illumination light and the image pickup light obtained when a lighting mode provided by light composed of laterally projected light and vertically projected light (hereinafter referred to as "fourth lighting mode" or "fourth illumination mode") is applied to the image pickup apparatus of FIG. 1. FIG. 7(b) is a schematic view showing the relationship between the composed light slit member selected for the fourth lighting mode and each of the illumination light and the image pickup light with respect to the specimen sample.

The fourth lighting mode, as shown in FIGS. 7(a) and 7(b), is carried out by a selective switching operation of the switching operation ring 32, so that the composed light slit member 71 of the illumination switching cylinder 31 faces the illumination light introducing section 13.

More particularly, in the fourth lighting mode, rays of illumination light (a), introduced into the illumination light introducing section 13 are permitted to pass through only the annular section of the focusing lens 72 of the composed light slit member 71, resulting in the light rays being parallel to each other. The light rays are then reflected by the annular mirror section 15 formed on the entire downwardly facing periphery of the half mirror member 14, to thereby be downwardly directed in the form of laterally projected light $a_{4a}$ in the direction of the central optical axis A, as in the first illumination mode described above. In addition, the rays are permitted to pass through the central section of the focusing lens 72 of the composed light slit member 71, resulting in the light rays being parallel to each other. These light rays are then reflected by the half mirror section 16 formed at the central section of the half mirror member 14, to thereby be downwardly directed in the form of vertically projected light $a_{4b}$ in the direction of the central optical axis A, as in the third illumination mode described above.

The rays of the laterally projected light $a_{4a}$ are permitted to pass through the annular converging lens 18, and are then introduced from annular the converging step 21 into the converging guide member 19, so that the observed section of the specimen sample C is illuminated with the light $a_{4a}$ discharged in an entire or full circumferential direction from the objective opening 20. In addition, rays of the vertically projected light $a_{4b}$ are permitted to pass through the image pickup optical system 17, so that the observed section of the specimen sample C is illuminated with the light $a_{4b}$ vertically discharged through the objective opening 20. Thus, the observed section of the specimen sample C is independently illuminated with the laterally projected light $a_{4a}$ in the whole or full circumferential direction and with the vertically projected light $a_{4b}$ in the vertical direction. In other words, it is independently irradiated with light $a_4$ composed of the laterally projected light $a_{4a}$ and vertically projected light $a_{4b}$.

The image pickup light $b_4$ reflected by the observed section of the specimen sample C is guided from the objective opening 20 through the image pickup optical system 17 to the half mirror section 16 of the half mirror member 14, and is then introduced into the CCD element 24. The CCD element 24 converts the image pickup light $b_4$ into an electrical signal, which is then displayed on a TV monitor (not shown). This results in an image of the observed section of the specimen sample C illuminated with the light $a_4$ composed of the laterally projected light $a_4$ and vertically projected light $a_4$ as desired, or the image illuminated in the fourth lighting mode is readily and effectively observed.

Referring now to FIGS. 11 and 12, a third embodiment of a lighting device for an observation/image pickup apparatus according to the present invention is illustrated. More specifically, FIGS. 11 and 12 each schematically show an image pickup apparatus to which a lighting device of the third embodiment is applied. The lighting device of the third embodiment is applied to an image pickup apparatus as in the first and second embodiments described above. However, it may also be effectively applied to an observation apparatus.

The lighting device of the third embodiment includes a lens tube 111, which is provided with a cylindrical barrel 112. The cylindrical barrel 112 is provided on a part of an outer periphery thereof with an illumination light introducing section 113 for permitting illumination light on an incident optical axis B transmitted through an optical fiber bundle 113a to be introduced therethrough into the lens tube 111. The illumination light introducing section 113 includes a focusing lens 114 for focusing illumination light. The focusing lens 114 is formed into an annular shape and is arranged along the incident optical axis 13 so as to permit only the full annular or circumferential portion of the illumination light introducing section 113 to act as a light permeable section, and the remaining central portion thereof acts as a light non-permeable section 115 for interrupting the illumination light. Thus, the focusing lens 114 functions to cause rays of illumination light introduced into the illumination light introducing section 113 to be parallel to each other while being kept wholly annular, with the light then guided into the cylindrical barrel 112.

The cylindrical barrel 112 is provided therein with a half mirror member 116. The half mirror member 116 is arranged in a manner to face the illumination light introducing section 113 while being kept oblique at an angle of 45 degrees on a central optical axis A, and is formed on a peripheral portion of a lower side (i.e., the downwardly facing surface) thereof with an annular mirror section 117 and at a central portion thereof with a half mirror section 118. The annular mirror section 117 is separately formed on the half mirror member 116 by deposition.

The lens tube 111 is provided therein with an observation optical system 119 which is arranged below the half mirror member 116 and which includes an objective lens arranged so as to positionally correspond to the half mirror section 118 of the half mirror member 116 along the central optical axis A. In addition, the lens tube 111 is provided therein with a converging guide member 120 which is arranged below the half mirror member and includes an outside optical path 121, an inside optical path 122 and an optical path switching damper 123 for switching between the outside optical path 121 and the inside optical path 122, which damper 123 is arranged on the upper light introducing surface of the converging guide member so as to be opposite to the annular mirror section 117. The converging guide member 120 is formed with an objective opening 124 associated with the downwardly extending outside optical path 121. The objective opening 124 is arranged so as to face a surface of an observed section of a specimen sample C on the central optical axis A. Further, the converging guide member 120 is formed with a lower opening 125 disposed or arranged to be directed toward the specimen sample C.

The lens tube 111 also includes a focus mechanism 126 arranged on the cylindrical barrel 112 so as to constitute an upper section of the lens tube 111. The focus mechanism 126 is actuated for focusing by means of a focus operation ring 127. The focus mechanism 126 is provided therein with a CCD element 128, which is positioned on the central optical axis A and includes a variable magnifying mechanism 129.

Now, the manner of operation of the third embodiment constructed as described above will be described hereinafter.

The following description will be made on the assumption that the specimen sample C, arranged so as to face the objective opening 124 of the lens tube 111, has been subjected to a focusing operation by the focus mechanism 126 through the focus operation ring 127, and a magnification varying operation by the variable magnification mechanism 129 in each of the illumination modes, and the image pickup light b obtained by lighting the specimen sample C in each of the illumination modes is set so as to properly enter the CCD element 128.

FIG. 11 is a vertical sectional view showing an optical path of each of the illumination light and the image pickup light obtained when a lighting mode provided by laterally projected light (hereinafter referred to as "fifth lighting mode" or "fifth illumination mode") is applied to the image pickup apparatus of the third embodiment described above.

In the fifth lighting mode, as shown in FIG. 11, a selective switching operation of the optical path switching damper 123 toward the inside optical path 122 results in the outside optical path 121 of the converging guide member 120 being utilized. Switching of the optical path switching damper 123 toward the inside optical path 122 corresponds to lighting of the specimen sample C by laterally projected light introduced into the outside optical path 121.

More particularly, in the fifth lighting mode, rays of illumination light (a), introduced into the illumination light introducing section 113, are permitted to pass through the focusing lens 114, resulting in the rays being rendered parallel to each other. The light is then totally reflected by the annular mirror section 117 of the half mirror member 116, to thereby be guided to an upper light-guide side of the converging guide member 120. Then, the rays are introduced into the outside optical path 121, and then are repeatedly reflected by an outer switching surface of the optical path switching damper 123, as well as an inner surface of the outside optical path 121 in the outside optical path 121. Subsequently, the rays are projected in the form of laterally projected light $a_5$ on the observed section of the specimen sample C from a whole or entire circumference of the objective opening 124. Thus, the observed section of the specimen sample C is independently illuminated with the laterally projected light $a_5$ in a whole or full circumferential direction.

Then, image pickup light $b_5$ reflected by the observed section of the specimen sample C is guided from the objective opening 124 through the observation optical system 119 to the half mirror section 118 of the half mirror member 116 and then introduced into the CCD element 128, so that the CCD element 128 converts the image pickup light $b_5$ into an electrical signal, which is then displayed on a TV monitor (not shown). This results in an image of the observed section of the specimen sample C illuminated with the laterally projected light $a_5$ as desired, or the image illuminated in the fifth lighting mode is readily and effectively observed.

FIG. 12 is a vertical sectional view showing an optical path of each of the illumination light and the image pickup light obtained when a lighting mode provided by vertically projected light (hereinafter referred to as "sixth lighting mode" or "sixth illumination mode") is applied to the image pickup apparatus of the third embodiment described above.

In the sixth lighting mode, as shown in FIG. 12, a selective switching operation of the optical path switching damper 123 toward the outside optical path results in the inside optical path 122 of the converging guide member 120 being utilized. Switching of the optical path switching damper 123 toward the outside optical path 121 corresponds to lighting of the specimen sample C by vertically projected light introduced into the inside optical path 122.

More particularly, in the sixth lighting mode, rays of the illumination light (a), introduced into the illumination light introducing section 113, are permitted to pass through the focusing lens 114, resulting in the light rays being rendered parallel to each other. The light is then totally reflected by the annular mirror section 117 of the half mirror member 116, to thereby be guided to the upper light-guide side of the converging guide member 120, resulting in the light being introduced into the inside optical path 122. Then, the rays are repeatedly reflected by an inner switching surface of the optical path switching damper 123, as well as the inner surface of the inside optical path 122 in the inside optical path 122. Subsequently, the rays are projected in the form of vertically projected light $a_6$ on the observed section of the specimen sample C from an entire circumference of the lower opening 125. Thus, the observed section of the specimen sample C is independently illuminated with the vertically projected light $a_6$ in a whole or full circumferential direction.

Then, image pickup light $b_6$ reflected by the observed section of the specimen sample C is guided from the objective opening 124 through the observation optical system 119 to the half mirror section 118 of the half mirror member 116 and then introduced into the CCD element 128. The CCD element 128 converts the image pickup light $b_6$ into an electrical signal, which is then displayed on a TV monitor (not shown). This results in an image of the observed section of the specimen sample C illuminated with the vertically projected light $a_6$ as desired, or the image illuminated in the sixth lighting mode is readily and effectively observed.

In each of the first to third embodiments described above, the illumination control slit member is provided with the converging lens for providing parallel rays. Alternatively, any desired optical system for rendering rays of illumination light parallel is interposedly arranged between the slit member and the illumination light introducing section, resulting in a light guide slit being substituted for the converging lens.

Obviously additional modifications and variations are possible in light of the above teachings. It is therefore to be understood that within the scope of the appended claims, the invention may be practiced otherwise than as specifically described.

What is claimed as new and is desired to be secured by Letters Patent of the United States is:

1. A lighting device for an observation/image pickup apparatus, comprising:
   a lens tube including a cylindrical barrel, said cylindrical barrel including an illumination light introducing section which permits illumination light to be introduced into said lens tube;
   a half mirror member disposed in said cylindrical barrel, said half mirror member facing said illumination light introducing section and disposed at a predetermined angle with respect to a central optical axis;

said half mirror member including an annular mirror section at a peripheral portion of the half mirror member, and a half mirror section at a central portion of said half mirror member;

an illumination switching cylinder disposed in said lens tube, said illumination switching cylinder being rotatable and surrounding said half mirror member about said central optical axis;

an image pickup optical system arranged below said half mirror member and including an objective lens arranged so as to positionally correspond to said half mirror section along said central optical axis;

an annular converging lens arranged below said half mirror member and positionally corresponding to said annular mirror section; and a converging guide member arranged below said image pickup optical system and annular converging lens, said converging guide member disposed to positionally correspond to said annular converging lens;

said converging guide member including an objective opening facing a surface of an observed section of a specimen sample on said central optical axis;

said illumination switching cylinder being provided on a periphery thereof with a plurality of illumination control slit members for respectively permitting illumination light introduced into said lens tube through said illumination light introducing section to be selectively converted into at least: laterally projected light, deflected oblique light, vertically projected light, and light composed of laterally projected light and vertically projected light;

said illumination control slit members being arranged to selectively face said illumination light introducing section.

2. A lighting device as defined in claim 1, wherein said illumination control slit members each include a focusing optical system for rendering rays of illumination light introduced through said illumination light introducing section parallel to each other.

3. A lighting device as defined in claim 1 or 2, wherein said illumination control slit member for laterally projected light is provided with a focusing lens acting as a light permeable section at only a portion thereof corresponding to said annular mirror section.

4. A lighting device as defined in claim 1 or 2, wherein said illumination control slit member for deflected oblique light is provided with a focusing lens acting as a light permeable section at only a portion thereof corresponding to a part of said annular mirror section.

5. A lighting device as defined in claim 1 or 2, wherein said illumination control slit member for vertically projected light is provided with a focusing lens acting as a light permeable section at only a portion thereof corresponding to a part of said half mirror section.

6. A lighting device as defined in claim 1 or 2, wherein said illumination control slit member for light composed of laterally projected light and vertically projected light is provided with a focusing lens acting as a light permeable section at only a portion thereof corresponding to each of said annular mirror section and half mirror section.

7. A lighting device for an observation/image pickup apparatus, comprising:

a lens tube including a cylindrical barrel, said cylindrical barrel including an illumination light introducing section which permits illumination light to be introduced into said lens tube;

a half mirror member disposed in said cylindrical barrel, said half mirror member facing said illumination light introducing section at a predetermined angle with respect to a central optical axis;

said half mirror member including an annular mirror section at a peripheral portion of the half mirror member, and a half mirror section at a central portion of the half mirror member;

an illumination switching cylinder disposed in said lens tube, said illumination switching cylinder being rotatable and surrounding said half mirror member about said central optical axis;

an image pickup optical system arranged below said half mirror member and including an objective lens arranged so as to positionally correspond to said half mirror section along said central optical axis;

an annular converging lens arranged below said half mirror member and positionally corresponding to said annular mirror section; and a converging guide member arranged below said image pickup optical system and annular converging lens, said converging guide member disposed to positionally correspond to said annular converging lens;

said converging guide member including an objective opening facing a surface of an observed section of a specimen sample on said central optical axis;

said illumination switching cylinder being provided on a periphery thereof with a plurality of illumination control slit members for respectively permitting illumination light introduced into said lens tube through said illumination light introducing section to be selectively converted into at least laterally projected light, deflected oblique light, vertically projected light and light composed of laterally projected light and vertically projected light;

said illumination control slit member for deflected oblique light being rotatable and disposed perpendicular to an incident optical axis of said illumination light introducing section;

said illumination control slit members being to selectively face said illumination light introducing section as desired, and when said illumination control slit member for deflected oblique light is selected, said illumination control slit member for deflected oblique light is selectively rotated about the incident optical axis of said illumination light introducing section to set an angle of deflected oblique light with respect to the specimen sample.

8. A lighting device as defined in claim 7, wherein said illumination control slit members each include a focusing optical system for rendering rays of illumination light introduced through said illumination light introducing section parallel to each other.

9. A lighting device as defined in claim 7 or 8, wherein said illumination control slit member for laterally projected light is provided with a focusing lens acting as a light permeable section at only a portion thereof corresponding to said annular mirror section.

10. A lighting device as defined in claim 7 or 8, wherein said illumination control slit member for deflected oblique light is provided with a focusing lens acting as a light permeable section at only a portion thereof corresponding to a part of said annular mirror section.

11. A lighting device as defined in claim 7 or 8, wherein said illumination control slit member for vertically projected light is provided with a focusing lens acting as a light permeable section at only a portion thereof corresponding to a part of said half mirror section.

12. A lighting device as defined in claim 7 or 8, wherein said illumination control slit member for light composed of laterally projected light and vertically projected light is provided with a focusing lens acting as a light permeable section at only a portion thereof corresponding to each of said annular mirror section and half mirror section.

13. A lighting device for an observation/image pickup apparatus, comprising:

- a lens tube including a cylindrical barrel, said cylindrical barrel including an illumination light introducing section which permits illumination light to be introduced into said lens tube;
- a half mirror member disposed in said cylindrical barrel, said half mirror member facing said illumination light introducing section at a predetermined angle with respect to a central optical axis;
- said half mirror member including an annular mirror section at a peripheral portion of said half mirror member, and a half mirror section at a central portion of said half mirror member;
- an observation optical system arranged below said half mirror member and including an objective lens disposed to positionally correspond to said half mirror section along said central optical axis;
- a converging guide member including an outside optical path, an inside optical path, and an optical path switching damper arranged on an upper light-guide side of said half mirror member opposite to said annular mirror section for carrying out switching between the outside optical path and the inside optical path;
- said outside optical path being provided with an objective opening facing a surface of an observed section of a specimen sample, and said inside optical path being provided with a lower opening directed toward the specimen sample;
- said optical path switching damper being switched toward said inside optical path to permit illumination light introduced into said outside optical path to be applied in the form of laterally projected light from an inner periphery of said objective opening to the specimen sample, and switched toward said outside optical path to permit illumination light introduced into said inside optical path to be applied in the form of vertically projected light from said lower opening to the specimen sample.

14. A light guide device as defined in claim 13 wherein said illumination light introducing section is provided with a focussing lens acting as a light permeable section at only a portion thereof corresponding to said annular mirror section and a light non-permeable section is provided at said illumination light introducing section so as to positionally correspond to said half mirror section.

* * * * *